(12) United States Patent
Yamamoto et al.

(10) Patent No.: US 8,178,290 B2
(45) Date of Patent: May 15, 2012

(54) SOLID SUPPORT

(75) Inventors: Noriaki Yamamoto, Tokyo (JP); Keigo Tamaki, Tokyo (JP); Koji Miyazaki, Tokyo (JP); Akihisa Nakajima, Tokyo (JP)

(73) Assignee: Konica Minolta Medical & Graphic, Inc., Tokyo (JE)

( * ) Notice: Subject to any disclaimer, the term of this patent is extended or adjusted under 35 U.S.C. 154(b) by 0 days.

(21) Appl. No.: 13/110,473

(22) Filed: May 18, 2011

(65) Prior Publication Data

US 2011/0224420 A1 Sep. 15, 2011

Related U.S. Application Data

(62) Division of application No. 12/212,839, filed on Sep. 18, 2008, now abandoned.

(30) Foreign Application Priority Data

Nov. 20, 2007 (JP) .................. 2007-300536
Jan. 8, 2008 (JP) .................. 2008-001616

(51) Int. Cl.
*C12Q 1/24* (2006.01)
*C12Q 1/68* (2006.01)

(52) U.S. Cl. ................................. 435/4; 435/6
(58) Field of Classification Search .................. None
See application file for complete search history.

(56) References Cited

OTHER PUBLICATIONS

Furugen et al. (Microb. Pathogenesis, 30:129-138, 2001).*
Andreassen (Immunodiagnostics, 2005).*

* cited by examiner

*Primary Examiner* — Nita M Minnifield
*Assistant Examiner* — Brian J Gangle
(74) *Attorney, Agent, or Firm* — Lucas & Mercanti, LLP

(57) ABSTRACT

The present invention provides a solid support for performing steps of isolation of cell or extraction and purification of nucleic acid, safely, easily, efficiently, and with high yield in the genetic test for investigating the presence of pathogenic bacterial infection. A solid support for binding with cell as an embodiment of the above-described solid support, comprises a polypeptide having capability of binding with my colic acid-containing glycolipid which is immobilized on the surface of a carrier. In addition, a solid support for binding with nucleic acid as another embodiment of the above-described solid support, comprises a polypeptide having capability of binding with nucleic acid which is immobilized on the surface of a carrier.

11 Claims, No Drawings

SOLID SUPPORT

CROSS REFERENCE TO RELATED APPLICATIONS

This is a Divisional Application of U.S. application Ser. No. 12/212,839 filed Sep. 18, 2008 which, in turn, claimed the priority of Japanese Applications 2007-300536 filed Nov. 20, 2007 and 2008-001616 filed January 2008, the priority of all three Applications hereby claimed and the contents of each of the three Applications are incorporated herein by reference.

BACKGROUND OF THE INVENTION

1. Field of the Invention

The present invention relates to a solid support. More specifically, the present Invention relates to a solid support comprising a polypeptide which is immobilized on the surface of a carrier.

2. Description of Related Art

Genetic test for investigating the presence of pathogenic bacterial infection is carried out by determining the presence of nucleic acid derived from the pathogenic bacteria in a clinical sample collected from patient. The testing process comprises mainly the following 3 steps: (1) collecting of pathogenic bacteria (solution of cell); (2) bacteriolysis (extraction and purification of nucleic acid); and (3) gene amplification and detection. Yield of the pathogenic bacterial cell and/or the nucleic acid in each step affects greatly on sensitivity and accuracy of the test.

In the above-described step (1) of collecting a pathogenic bacteria, when, for example, tuberculosis bacteria is collected as the pathogenic bacteria, collection of the tuberculosis bacteria has been carried out conventionally by a high-speed centrifugal separation procedure. However, the high-speed centrifugal separation procedure is known to have the following problems: Firstly, in the high-speed centrifugal separation procedure, generation of aerosol tends to take place, and opening and closing operations of the sample container is required. Therefore, there is a possibility of cross-contamination to occur between samples, and in addition, there are concerns about biohazard such as contact infection of operator, environmental pollution and the like. Secondly, since the procedure requires a relatively large stand alone instrument of a high-speed centrifugal separator, it is difficult to automate a series of the above-described test steps in a continuous fashion. Thirdly, it takes long time for the high-speed centrifugation to attain a high recovery efficiency.

As an alternative method to such high-speed centrifugal separation procedure, a cell-collection technique for isolating pathogenic bacteria such as tuberculosis bacteria safely and easily within a short time using a solid support with polysaccharide as a ligand has been developed. It has been described that, in particular, when magnetic beads are used as a support (carrier), cell-collection can be performed easily by solid-liquid separation utilizing magnetic action (US-A-2003/153028).

In addition, in the above-described step (2) of bacteriolysis (extraction and purification of nucleic acid), after the bacterial cells collected by the step (1) or the like are lysed by a suitable method, nucleic acid is needed to be extracted and purified from the sample containing inhibitors of nucleic acid amplification reaction such as enzymes, other proteins, polysaccharides and lipids, and other contaminants. As to method for extracting a nucleic acid from a sample containing the same, for example, phenol/chloroform extraction method and the like have been used widely. After that, as a method for recovering the nucleic acid from a solution of phenol/chloroform extracts, ethanol precipitation method has been employed.

Further, method for purifying the extracted nucleic acid includes a method in which the nucleic acid is adsorbed on the surface of an adsorbent such as silica dioxide, silica polymer, magnesium silicate and the like, washed, and then the nucleic acid is desorbed (see, for example, JP-B-7(1995)-51065 and US-A-2004/235034). The method is excellent in separation performance of the adsorbent, however, the method has problems such as a difficulty in manufacturing the adsorbent with the same performance industrially on a large scale, and a difficulty in processing the adsorbent to various forms due to its inconvenient handling. And so, a method for separating and purifying nucleic acid has been developed, which comprises a step in which nucleic acid is adsorbed on or desorbed from a solid phase made of a surface-saponified product of acetylcellulose (an organic macromolecule having hydroxyl group on the surface) instead of the above-described adsorbents of silicon oxide type. According to the technology, it is stated that the surface-saponified product of acetylcellulose is excellent in separation performance, good in washing efficiency, and easy in workability compared with the adsorbent of silicon oxide type, and capable of being produced on a large scale with a substantially equivalent separation performance (US-A-2003/170664). However, in either method described above, there remain such problems that it is necessary to use chaotropic agent such as perchloric acid when the nucleic acid is trapped on the adsorbent, and further that a mixed solution of solubilized nucleic acid is required to be mixed with water-soluble organic solvent, and the resultant mixed solution of nucleic acid requires existence of a salt. A method of avoiding the use of hazardous reagent such as chaotropic agents by employing porous carrier (glass fiber, cellulose fiber, hydroxyapatite, and the like) capable of adsorbing nucleic acid has also been developed (JP-A-2005-80555). However, since the method comprises drying step, operation is cumbersome and requires large-sized equipment. On the other hand, in recent years, for the nucleic acid extracted from tissue, a method for recovering mRNA and the like by using a carrier on which an oligo dT sequence is immobilized, has been developed (US-A-2007/092576).

Aside from the above-described isolation techniques of nucleic acid from pathogenic bacteria, MDP1 (*Mycobacterium* DNA-Binding Protein 1) which is a polypeptide having immunogenicity against pathogenic acid-fast bacteria, and utilization thereof for a vaccine or a therapeutic agent has been disclosed (WO 2000/44905).

BRIEF SUMMARY OF THE INVENTION

However, the cell-collection method using a solid support described in US-A-2003/153028 has a problem that the cell-collection efficiency is lower as compared to the high-speed centrifugal separation method because the method utilizes nonspecific interaction between proteins on the cell wall of bacteria and a polysaccharide immobilized on a carrier, and has a difficulty in performing cell-collection of a specified bacterial cell in high yield. In addition, in the method for purifying a nucleic acid, there also remain problems such as cumbersome operation and a difficulty to attain a desired yield. From such background, further improvement in the steps of cell collection or extraction and purification of nucleic acid in genetic test for investigation of the presence of pathogenic bacterial infection has been demanded.

Therefore, it is an object of the present invention to provide a solid support for performing the steps of isolation and collection of bacterial cell or extraction and purification of nucleic acid, safely, easily, efficiently, and with high yield, in the genetic test for investigation of the presence of pathogenic bacterial infection.

The present inventors have studied intensively to solve the above-described problems. As a result, the present inventors have found that, by using a solid support comprising a polypeptide having a binding capability with mycolic acid-containing glycolipids or nucleic acid contained in the cell wall of pathogenic bacteria which is immobilized on the solid support, isolation of bacterial cell or extraction and purification of nucleic acid in the genetic test can be performed safely, easily, efficiently, and with high yield, and have thus completed the present invention.

That is, a solid support of an aspect of the present invention for achieving the above-described purpose is the one comprising a polypeptide having a binding capability with mycotic acid-containing glycolipids which is immobilized on the surface of a carrier.

In addition, another aspect of solid support of the present invention for achieving the above-described object is the one comprising a polypeptide having a binding capability with nucleic acid which is immobilized on the surface of a carrier.

According to one aspect of the solid support of the present invention, isolation of pathogenic bacteria containing mycotic acid-containing glycolipids in the cell wall from clinical sample can be performed safely, easily, efficiently, and with high yield. To be brief, high-sensitive and highly accurate test can be performed without apprehension of contamination and biohazards or requirement of cumbersome operations, in contrast to the traditional methods.

In addition, according to another aspect of solid support of the present invention, extraction and purification of nucleic acid can be performed safely, easily, efficiently, and with high yield. That is, since use of hazardous reagents such as chaotropic reagents and organic solvents in the traditional methods is avoided, the purification step is safe as a whole, and substantially no denaturation of isolated nucleic acid is observed. Further, high-sensitive and highly-accurate test can be performed without carrying out such operations as centrifugal separation, filtration, and treatment under reduced pressure.

Other objects, characteristics, and advantages of the present invention will become clear by referring to preferable aspects illustrated in the following descriptions.

DETAILED DESCRIPTION OF THE INVENTION

[ Solid Support]

The solid support involved in one embodiment of the present invention is the one in which a polypeptide having a binding capability with mycolic acid-containing glycolipids is immobilized on the surface of a carrier. According to the solid support (hereinafter, sometimes referred to as "solid support for cell binding"), the mycolic acid-containing glycolipids present in the cell wall of bacterial cell is bound to the polypeptide immobilized on the surface of a carrier of the solid support, and the solid support binding with bacterial cell may be obtained. By taking up this solid support binding with bacterial cell from a sample solution, the cells can be isolated. And, after isolation of the cell, nucleic acid is released by applying bacteriolytic treatment to the cells bound to the solid support, and the nucleic acid can be extracted by removing the cell wall of the bacteria bound to the solid support.

In addition, the solid support involved in another embodiment of the present invention is the one in which a polypeptide having a binding capability with nucleic acid is immobilized on the surface of a carrier. According to the solid support (hereinafter, sometimes referred to as "solid support for nucleic acid binding"), nucleic acid is bound to the immobilized polypeptide on the surface of a carrier of the solid support, and the solid support binding with nucleic acid may be obtained. By taking up this solid support binding with nucleic acid from a sample solution, the nucleic acid can be obtained with a high purity.

(Polypeptide)

The polypeptide in the above-described solid support for cell binding has a binding capability with the mycolic acid-containing glycolipids. In the present invention, "polypeptide" is a polymer molecule of amino acids polymerized by peptide bond, including proteins with higher-order structures and modified proteins. In addition, in the present invention, the term "binding" means ionic bond, hydrogen bond and the like, as well as adhesion and adsorption by intermolecular interactions such as dipole-dipole interaction, van der Waal's force, and hydrophobic interaction. As the polypeptide, any kind of polypeptides may be used without any particular limitation, so long as the polypeptide has a binding capability with the mycolic acid-containing glycolipids. The mycolic acid-containing glycolipids are the glycolipid contained in the cell wall of *Mycobacterium* genus (acid-fast bacteria) and its closely-related species such as *Nocardia* genus, *Rhodococcus* genus and the like, and generally reside in a form of a mixture of analogs having various molecular weights. In the genus *Mycobacterium* (acid-fast bacteria), pathogenic and cytozoic bacteria such as human tubercle bacillus (*Mycobacterium tuberculosis*) and Hansen's bacillus (*Mycobacterium leprae*) are included, and its very slow growth makes intracellular parasitism and acquisition of drug resistance possible. As to the mycolic acid-containing glycolipids, for example, avimycolic acid I, hominomycolic acid I, mycolic acid IIa, mycotic acid IIb, mycolic acid IIIa, mycolic acid IIIb, corynomycolic acid, trehalose-6-monomycolate, trehalose-6,6'-dimycolate, and meromycolic acid are known. Among them, trehalose-6,6'-dimycolate, in which 2 molecules of mycolic acid are linked via ester linkage at 6 and 6' positions of trehalose, is a specific glycolipid for acid-fast bacteria, and is a principal glycolipid which characterizes the cell wall of *Mycobacterium* genus.

The polypeptide in the above-described solid support for nucleic acid binding has a binding capability with nucleic acid when the polypeptide is not binding with mycolic acid-containing glycolipid such as trehalose-6,6'-dimycolate. That is, the polypeptide may bind with nucleic acid by a high affinity via noncovalent interaction such as hydrogen bond, ionic bond or hydrophobic interaction. Herein, "nucleic acid" means DNA, RNA, and polynucleotide containing modified nucleic acid base, and it may be a combination of these polynucleotides, regardless of single strand or double strand (partial double strand or single strand), and further includes peptide nucleic acid (PNA) and the like. The polypeptide having a capability of binding with nucleic acid is not particularly limited, so long as the polypeptide is known one having a capability of reversible adsorption and desorption, and known nucleic acid-binding protein such as DNA binding protein, RNA binding protein and the like may be suitably employed. Available nucleic acid-binding protein includes, generically for example, proteins of histone type (or histone-like proteins), transcription factor, nucleic acid repair protein (poly(ADP-ribose)polymerase (PARP) Ku protein and so on), and ribosomal protein. Type of the transcription factor involved in the transcriptional regulation such as onset, extension and termination of transcription through binding with DNA is over 50 types. The DNA binding protein includes, in particular, known transcription factor cro protein from λ phage, ATF 2, c-Fos, DP-1, c-Myb, c/EBP, CREB, FosB, E2F-1, c-Myc, Egr-1, c-Jun, E2F-2, Infl 1, Infl 2, Onc 1, Onc 2, Onc 3, Max, HIF-1α, c-Rel, JunD, Rb, USF 1, HIF-1β, NFκB p50, Sp-1, p107, USF2, Oct I, NFκB p65, STAT1, Sp-1, p53, and Oct II. It should be noted that, the term "DNA binding protein" used herein means, without limitation to narrow-defined "DNA binding protein" with known physiological significance, proteins which affect on the function of DNA by binding specifically to a particular site on DNA molecule in the nucleus of the cell, or by direct and specific interaction with the DNA. These proteins play a central role in activity of normal cell as a transcription factor to initiate gene expression, as a steroid hormone receptor to provide a specialized function, and as a DNA repair protein to maintain integrity of the genome. In addition, the RNA binding protein includes DRBP (dsRNA binding proteins) and the like, and specifically, for example, DRBP76 and RAX are included. In the present invention, the above-described "nucleic acid-binding protein" may be the one which is prepared in any method, It may be, for example, a genetically-engineered protein which is expressed in a test tube by known genetic engineering procedure using a gene encoding the protein. Alternatively, a fraction containing the nuclear protein may be extracted from living organism or cell. Or alternatively, samples available from library of protein and peptide may be used. The polypeptide having a capability of binding with nucleic acid also includes a polypeptide which may be obtained from the above-described "nucleic acid-binding protein" by chemical modification, partial cleavage (protease partial digestion, cyanogen bromide cleavage, reduction of disulfhydryl group) and the like, and retains nucleic acid binding capability.

The polypeptide to be used for the solid support for cell binding or the solid support for nucleic acid binding preferably has a binding capability with both mycolic acid-containing glycolipid and nucleic acid. By using such polypeptide, isolation of pathogenic bacterial cell and extraction and purification of nucleic acid in the bacteria in genetic test can be performed with a single type of solid support. The polypeptide can be used without any particular limitation, so long as the polypeptide has a capability of binding with both mycolic acid-containing glycolipid and nucleic acid. Such polypeptide includes, for example, MDP1 (*Mycobacterium* DNA-Binding Protein 1) isolated from BCG Tokyo strain belonging to *Mycobacterium* genus.

MDP1 is a histone-like protein specific for acid-fast bacteria, and capable of binding with both DNA and RNA by recognizing conformation of the nucleic acid. In addition, the MDP1 has been reported to be a cause of delayed growth of acid-fast bacteria through involvement in the regulation of gene expression (WO 2000/44905). The MDP1 is known to be present in the cell wall of tuberculosis bacteria and the like, and to interact strongly with glycosaminoglycan. Further, from the study of the present inventors, it has been shown that the mycolic acid-containing glycolipid of a cell wall component of tuberculosis bacteria interacts strongly with free MDP1, and that there is a possibility of binding the mycolic acid-containing glycolipid with MDP1 actually in the cell wall. The MDP1 can be obtained from, but not limited to, BCG Tokyo strain, but it can also be obtained by isolation and purification from bacteria belonging to *Mycobacterium* genus such as BCG strain other than BCC Tokyo strain, tuberculosis bacteria and so on.

The MDP1 is a polypeptide having 205 amino acids, but may also include a polypeptide having replacement, addition or deletion of one or a plurality of, preferably one to several amino acids at a specific position or randomly (herein, these are also referred to "MDP1"). The range of "one to several" is not particularly limited, but means, for example, 1 to 20, preferably 1 to 10, more preferably 1 to 5, and furthermore preferably 1 to 3. Here, the "replacement", "addition" or "deletion" which is modifications of amino acid residue are used in the customary sense, and the modifications which retain function of the MDP1 is acceptable. Introduction of a mutation such as replacement, deletion and/or addition of amino acid can be achieved by using known technologies such as, for example, site-specific mutation/PCR method (S. N. Ho et al., Gene, 77, 51(1989); Kaoru Saigo and Yumiko Sana joint translation, Current Protocols, compact edition, Molecular Biology Experimental Protocol I, June 1997, Maruzen Co. Ltd.).

As an embodiment of the above-described MDP1, recombinant proteins such as 6× histidine fusion protein and GST fusion protein are used suitably. When such recombinant protein is intended to be prepared, at first, a DNA coding the protein has to be obtained. Method for obtaining the DNA coding MDP1, its nucleotide sequence and the like are described in WO 2000/44905. By introducing this DNA into a suitable expression system to express as a recombinant protein, and then the recombinant protein may be extracted and isolated by affinity chromatography. For example, a DNA coding MDP1 is incorporated into a suitable vector such as, for example, pQE30 or pGEX; and this vector is introduced into bacterial cell such as *E. coli*, BCG or yeast cell to allow transformation; and the transformant cell is cultured; thereby, desired polypeptide may be produced (WO 2000/44905).

The MDP1 has a nucleic acid binding activity through recognition of guanine (G) or cytosine (C). Consequently, the nucleic acid may bind with MDP1 on the surface of the immobilized support of the present invention through G or C in a sequence of the nucleic acid. An important point is that the MDP1 is excellent in trapping GC-rich nucleic acid specifically because the MDP1 recognizes G and C nucleotides.
(Carrier)

In the present invention, the carrier functions as a base material for immobilizing the above-described polypeptide. Hereinafter, preferable embodiments of the carrier will be illustrated, and the following embodiments can be employed without any particular limitation in the solid support for either cell binding or nucleic acid binding. The carrier is preferably made of water-insoluble material because separation by solid-liquid separation is carried out in the step of isolation of bacterial cell and extraction and purification of nucleic acid. The term "water-insoluble" used herein means, specifically, insoluble in water or any other aqueous solution. The carrier may include any known carrier (support) or matrix which is currently used widely or proposed for using for immobilization, separation and the like.

Material to be used for the carrier includes, for example, inorganic compounds, metals, metal oxides, organic compounds or composite materials by combining these materials. The carrier is not particularly limited in quality, shape and size, so long as it can bind with acid-fast bacterial cell. Preferable material is the one which provides a large surface area for cell binding or nucleic acid binding.

Specific material to be used for the carrier includes typically, but not limited to, macromolecular materials of organic polymer such as polystyrene, polypropylene, polyacrylate, polymethyl methacrylate, polyethylene, polyamide, and latex, inorganic substances such as glass, silica, silica dioxide, silicon nitride, zirconium oxide, aluminum oxide, sodium oxide, calcium oxide, magnesium oxide and zinc oxide, or metals such as stainless steel and zirconia. Among them, glass, silica, latex, or macromolecular materials are preferable, and above all, organic polymer, particularly polystyrene is preferable. Generally, these materials have irregular surface such as porous structure, and are able to be fabricated to various forms such as beads, fiber, web, or sintered body.

In addition to the case where whole carrier is composed of a single material, the carrier may be, if necessary, a hybrid body composed of a plurality of materials. For example, a particle, in which the core part is made of magnetic responsive material such as iron oxide or chromium oxide and the surface of the particle is coated with an organic polymer in order to correspond to automated analysis, is exemplified. Herein, the carrier comprising such magnetic responsive material is sometimes referred to as "magnetic carrier". Hereinafter, the solid support using the magnetic carrier as a carrier is sometimes referred to as "magnetic solid support".

Since the solid support comprising the magnetic carrier binding with cells can be separated (solid-liquid) and recovered from a sample solution easily by magnetic force, the magnetic carrier preferably comprises a magnetic substance such as paramagnetic substance, ferroparamagnetic substance or ferromagnetic substance, and more preferably comprises both or either of paramagnetic substance and ferroparamagnetic substance. Particularly, use of ferroparamagnetic substance is particularly preferable in that it has no or little residual magnetization.

Specific example of such magnetic substance includes ferrosoferric oxide ($Fe_3O_4$), γ-type iron sesquioxide ($\gamma\text{-}Fe_2O_3$), various types of ferrite, metals such as iron, manganese, cobalt and chromium and various types of alloyed metal containing cobalt, nickel and manganese, and among them, ferrosoferric oxide is particularly preferable. In addition, cobalt and nickel are preferable from the viewpoint of having affinity for histidine tag.

As to the magnetic carrier to be used in the present invention, it is preferable that the magnetic carrier has excellent magnetic separation characteristic (namely, magnetic separation performance within a short time) and can be re-dispersed by gentle up-and-down shaking.

Content of the magnetic substance in the magnetic carrier is defined as less than 70% by weight because content of non-magnetic substance is 30% by weight or more, but preferably 20 to 70% by weight, and more preferably 30 to 70% by weight. If the content of the magnetic substance is lower than 20% by weight, sufficient magnetic response is not exerted, and separation of the solid support by required magnetic force in a short time becomes sometimes difficult to achieve. On the other hand, if this content exceeds 70% by weight, an amount of the magnetic substance exposed on the surface of the carrier increases, and elusion of a component of the magnetic substance such as iron ion may occur, and may give adverse effect on the other materials when used. In addition, the carrier may sometimes get brittle and be unable to gain practical strength.

Heretofore, a method of cell separation using the solid support containing the magnetic carrier has been developed (US-A-2003/1530281. However, since these solid supports used sugars which are bound nonspecifically with protein in the cell wall of bacteria as a ligand, some bacteria among the bacterial cells were occasionally not adsorbed to the solid support. Even in the case where the cells were adsorbed, it was very difficult to collect only objective bacterial cells on the surface efficiently, if the binding was nonspecific one. In the present invention, to ensure the isolation of pathogenic acid-fast bacteria (especially, tuberculosis bacteria) having mycolic acid-containing glycolipid in the cell wall, the MDP1 is bound (preferably by covalent bond) on the surface of the support, as a group capable of binding with mycolic acid-containing glycolipid on the surface of carrier (preferably, magnetic carrier). Amount of the MDP1 to be immobilized may be set out appropriately based on the support material, immobilization method, required yield of nucleic acid and the like.

In addition, a number of methods for purifying nucleic acid using magnetic support as a solid support have also been developed until now. For example, as a method of separation without using harmful solvent, there is Boom method in which contaminants such as protein, lipid and the like are solubilized in an aqueous phase using chaotropic reagent, and nucleic acid is adsorbed to silica beads and recovered as a solid phase, after that, the nucleic acid is dissolved again in an aqueous phase (Boom et al., J. Clin. Microbiol., vol. 28, 495-50 (1990)). In this method, a chaotropic reagent such as perchloric acid is required. Therefore, most of the extracted nucleic acids are fragmented to small size. In a preferable embodiment of the present invention, to promote the binding of nucleic acid to the magnetic solid support using magnetic particles such as magnetic beads under physiological condition without using such a harmful reagent, MDP1 is immobilized (preferably by covalent bond) on the surface of the carrier as a group having affinity to nucleic acid, and allowed to bind through the immobilized MDP1. Amount of MDP1 to be immobilized may be set out appropriately based on the carrier material, immobilization method, required yield of nucleic acid and the like. As a preferable embodiment, in particular, preparation of a recombinant MDP1 (rMDP1) having histidine tag can be performed on the basis of genetic engineering technology. Its immobilization on the surface of the magnetic beads is performed by forming covalent bond with an activated group on the magnetic beads through the histidine tag.

Shape of the carrier to be used for the send support of the present invention includes, but not particularly limited to, granular, rod-like, plate-like, sheet, gel, membrane, fiber, capillary, strip, filter and the like, and granular is preferable. Granular carrier, for example, beads is generally preferable due to its great binding capability, and beads made of polymer are particularly preferable.

The carrier to be used for the solid support of the present invention is preferably granular form, and the conceivable granular form includes, for example, spherical form, ellipsoidal form, conical form, cubical form and rectangular form. Among them, carrier of the spherical particle is preferable from the viewpoints of easy manufacturing and easy rotary agitation of the solid support in various purification steps. Size of the carrier as a solid support for cell binding is 0.5 to 10 μm, preferably 2 to 6 μm in a mean particle diameter. In the case where the mean particle diameter is lower than 0.5 μm, the carrier comprising a magnetic substance as described above does not exert sufficient magnetic response, and it may take a quite long time to separate the solid support comprising the carrier, and it may require a considerably great magnetic force to separate it. On the other hand, in the case where the mean particle diameter exceeds 10 μm, the carrier becomes precipitable, and therefore, an agitation procedure in an aqueous medium is needed for trapping cell. In addition, as the surface area per mass of the carrier becomes smaller, it sometimes becomes difficult to trap sufficient amount of cell. It should be noted that the "particle diameter" means herein a maximal distance L among distances between 2 arbitrary points on the contour of particle. In addition, for the "mean particle diameter", a value is adopted, which is calculated as a mean value from diameters of particles observed in several to several tens of fields of view, using an observation means such as scanning electron microscope (SEM) and transmission electron microscope (TEM).

The solid support of the present invention can be prepared by immobilizing the above-described polypeptide on the surface of the above-described carrier. Method of immobilization is by applying traditionally known techniques. In a preferable embodiment of the solid support, where MDP1 is used as a polypeptide and magnetic beads are used as a carrier, the peptide is immobilized, for example, by immobilizing MDP1 covalently to a tosyl group of the magnetic beads through histidine tag. It is also possible to perform the immobilization by making a coordinate bond between cobalt or nickel of the magnetic beads and the histidine tag. In addition, the immobilization may be carried out by binding en amino group of the polypeptide covalently with a tosyl group or an epoxy group of the magnetic beads. The polypeptide can be immobilized by reacting an amino group of the polypeptide with a carboxyl group (anchored maleic anhydride and the like) exposed on the surface of the support to form an amide bond in the presence of a dehydrocondensing reagent such as water-soluble carbodiimide. It may be by a formation of thioether bond between an active maleimide group anchored to polystyrene and a sulfhydryl group of protein. Alternatively, it may be a method of adsorbing the polypeptide physically to latex particle of polystyrene type. It should be noted that, by selecting amount and type of polypeptide to be immobilized on the carrier by those of ordinary skill in the art, amount and specificity of cell or nucleic acid to be bound to the solid support can be changed appropriately.

[Method for Isolating Cell]

The method for isolating cell of the present invention is characterized by comprising a step in which the above-described solid support for cell binding is contacted with a sample containing bacterial cell having mycolic acid-containing glycolipid in the cell wall. According to the method for isolating cell of the present invention, the cells having mycolic acid-containing glycolipid in the cell wall can be isolated. The cell is not particularly limited, so long as it has mycolic acid-containing glycolipid in the cell wall, and for example, pathogenic acid-fast bacterial cell is preferable. The "pathogenic acid-fast bacteria" (hereinafter, sometimes simply referred to as "acid-fast bacteria") are gram-positive bacteria belonging to acid-fast bacillus (*Mycobacterium* sp.), and have pathogenicity. The method is particularly suitable for the isolation of microorganism cell belonging to *Mycobacterium* (*Mycobacterium* genus). The culturable acid-fast bacteria other than *M. tuberculosis* complex and *Mycobacterium leprae* (Hansen's bacillus) are sometimes referred to as atypical mycobacteria.

In the present invention, among acid-fast bacteria, in particular the following 4 species of *M. tuberculosis* complex are targeted: namely, human tubercle bacillus (*Mycobacterium tuberculosis*), bovine tubercle bacillus (*Mycobacterium bovis*), *Mycobacterium Africans*, and mouse tubercle bacillus (*Mycobacterium microti*). All of them fall into a group of slow growing bacteria, and since their genes are closely analogous, it is genetically impossible to discriminate them from each other. In addition to them, *M. avium, M. intracellularae, M. chelonae, M. marinum* and *M. paratuberculosis* are important from the epidemiological and clinical points of view.

In the method for isolating cell of the aspect, the pathogenic bacteria, for example, the pathogenic acid-fast bacterial cell contained in a sample solution is bound to the above-described solid support, preferably magnetic solid support comprising magnetic carrier such as magnetic beads, and then the cells are separated from the sample solution and impurities, and thus the pathogenic acid-fast bacterial cells are isolated.

Sample is not particularly limited, so long as it is a biologically derived sample containing the above-described bacterial cell, but a specimen derived from biological origin, culture solution or cell-containing solution is relevant thereto. The specimen derived from biological origin includes, for example, whole blood, plasma, serum, buffy coat, urine, fecal matter, saliva, expectorated sputum, cerebrospinal fluid, seminal fluid, tissue (for example, cancer tissue, the lymph node), cell culture solution (for example, bacterial culture) or solution containing cell, and almost all samples derived from biological object are relevant thereto. Form of the sample is preferably fluidic sample, usually liquid such as solution or suspension.

Specific operational procedures of the method for isolating cell in the present invention is exemplified by the following embodiments in which a magnetic solid support is used as the solid support, but not limited thereto. A sample containing cells and a magnetic solid support including a magnetic carrier (preferably, magnetic beads) are mixed and stirred, and thereby pathogenic acid-fast bacterial cells in the sample solution are allowed to bind to polypeptide (preferably, MDP1) immobilized on the surface of the magnetic carrier. On this occasion, to promote the binding of the cells to the magnetic solid support, a suitable binding buffer may be used. By conducting solid-liquid separation of the above-described magnetic solid support from the sample solution, impurities, undesired substances and the like can be separated and removed, and the magnetic solid support comprising the immobilized polypeptide binding the pathogenic acid-fast bacterial cell on the surface thereof can be obtained.

Next, it is preferable to remove further the impurities attached to the magnetic solid support by stirring the solid support together with the wash buffer, conducting washing procedure and subsequent another solid-liquid separation procedure. As mentioned above, a step of the solid-liquid separation is included in the present invention. On that occasion, method of solid-liquid separation is not particularly limited, but it includes, for example, methods using centrifugal separation procedure and magnetic action, and separation by magnetic action is preferable. More preferably, the solid-liquid separation is performed in a completely closed system by making magnetic force from an external magnet to act on a container for the magnetic solid support. According to the method, operation is easier than the centrifugal separation, and there is no risk of contamination.

In the case where the solid support is a magnetic solid support using magnetic beads, the magnetic solid support is preferably suspended at least in any one of the following stages: before mixing with sample solution, after mixing with sample solution, at the time of washing the magnetic solid support. Significance of making the Magnetic solid support suspended is as follows. Before mixing, the magnetic solid support agglutinates together during storage by the magnetic action of magnetic beads of the carrier. And so, if the magnetic solid support is dispersed by suspension, when mixed with a sample solution, contact area and contact frequency between the magnetic solid support and cell would be increased. If the suspension state is maintained after mixing with the sample, the magnetic solid support is kept dispersed in the sample solution by suspension, and contact area and contact frequency between the magnetic solid support and cell would be increased. In addition, on the occasion of washing, the magnetic solid support is dispersed in the wash buffer by suspension, contact area and contact frequency between the magnetic beads contained in the magnetic solid support (cells are attached on the surface) and effective substance for washing in the wash buffer would be increased. Due to such effects, improvements in amount and purity of cell and nucleic acid to be separated and recovered from sample solution in each step can be expected.

[Method for Extracting Nucleic Acid]

Method for extracting nucleic acid of the present invention is characterized by comprising a step in which cells are isolated by contacting the above-described solid support for cell binding with a sample containing bacterial cells having mycolic acid-containing glycolipid in the cell wall, and a step in which nucleic acid in the isolated cell is extracted.

In the present invention, the step in which cells are isolated by contacting the above-described solid support with a sample containing bacterial cells having mycolic acid-containing glycolipid in the cell wall can be carried out by the same method as used in the above-described method for isolation of cell, therefore, explanation is skipped here. In the subsequent step of the extraction of nucleic acid in the isolated cell, cell wall and biological membrane such as cell membrane and nuclear membrane of the bacterial cells, in the state being bound to the solid support, are disrupted (bacteriolysis) by ultrasonic treatment, heating or chemical treatment to release the nucleic acid to outside of the cell; the solid support bound with cell well is removed; residual solution is separated and recovered as a nucleic acid solution. In this method, since operations such as filtration and treatment under reduced pressure are not included, isolation of nucleic acid can be performed easily and speedy. Further, when the magnetic solid support is employed, solid-liquid separation can be performed without conducting centrifugal separation operation.

The above-described disruption of cell wall and biological membranes can be performed using various known physical or chemical methods. In the physical method, ultrasonic treatment, freezing and thawing method, heating method and so on are included, and as the chemical method, treatment with chemical reagent, for example, enzymatic digestion method, denaturation method using chaotropic reagent, surface active agent or bacteriolytic agent are known. In Table 1 and 2 of U.S. Pat. No. 5,376,527, various kinds of protocols for bacteriolysis of cells such as *Mycobacterium* have been collected.

In the method of the present invention, as the bacteriolytic treatment, the disruption of cell membrane is carried out preferably by physical method such as ultrasonic irradiation method, freezing and thawing method and heating method, by treatment with chemical reagents, or by the combination thereof. In particular, physical method is desirable because its operation is simple, while treatment with chemical reagents is required to remove the agents (chaotropic reagent, surface active agent, or bacteriolytic agent) used for the disruption of cell membrane afterward. Unless such reagent which may affect adversely on reaction or treatment to be carried out in the subsequent steps is used, the isolated nucleic acid can be applied directly to DNA amplification reaction, hybridization, restriction enzyme reaction, detection reaction or electrophoretic analysis, and so on. Therefore, even if the sample is of trace amount, the nucleic acid can be isolated from cells with high yield according to the method of the present invention.

The above-described ultrasonic treatment, heat treatment, and combination treatment of ultrasonic wave and heating are effective treatment conditions for bacteriolysis, and are conducted within a range where at least the nucleic acid does not cause denaturation by the ultrasonic wave or heat. In the case of ultrasonic treatment, effective irradiation condition and irradiation time for bacteriolysis are set out adequately. Irradiation quantity can be calculated from declared power of ultrasonic dispersion equipment, volume of suspension to be irradiated and irradiation time. For example, ultrasonic intensity is selected by volume of formulation, stirring condition and the like, but irradiation of frequency 10 to 100 kHz, preferably 15 to 45 kHz for at least 5 minutes, preferably about 5 to 30 minutes, is preferable. In the case of heat treatment, heating is conducted at temperature range, namely 70 to 120° C., preferably 80 to 120° C., more preferably 80 to 100° C., for 20 seconds to 10 minutes, preferably 20 to 300 seconds. The heating conditions (temperature and time) are variable depending on type of cell or bacteria (size, composition and thickness of the cell membrane), and is selected appropriately within the above-described ranges. Heating may be carried out by any kinds of suitable heating methods, and dry heating block, hot-water bath, microwave oven, various types of heating medium and the like are exemplified. However, it should not be limited thereto. The preferable treatment for releasing nucleic acid by lysing the above-described pathogenic acid-fast bacterial cell is an embodiment of the treatment by heating and ultrasonic irradiation. In the combined treatment by combination of ultrasonic irradiation and heating, the bacteriolysis can be performed under further gentle treatment condition compared to that in the above-described each treatment.

[Method for Purifying Nucleic Acid]

The method for purifying nucleic acid of the present invention is characterized by comprising a step in which the above-described solid support for nucleic acid binding is contacted with a sample containing nucleic acid.

The nucleic acid to be targeted in the method for isolating in the present invention is DNA or RNA, wherein DNA includes genomic DNA, cDNA and the like, and RNA includes mRNA, tRNA, rRNA and the like. Further, these nucleic acids may be irrespective of single stranded or double stranded. Quantity of DNA to be isolated is 0.0005 ng to 2 mg, and suitable range includes 0.001 ng to 1 mg (200 to $2 \times 10^{11}$ copies).

The sample containing nucleic acid to be targeted for purification includes a solution containing nucleic acid extracted by cell lysis, a solution containing nucleic acid extracted from running gel after electrophoresis, nucleic acid-containing solution after enzyme reaction, and the like. Here, the solution containing nucleic acid extracted by cell lysis is a solution containing nucleic acid extracted from biologically derived specimen, culture solution or cell-containing solution, in which the nucleic acid released by cell membrane-disruption treatment is present. The biologically derived specimen is not particularly limited, and includes test substances widely containing cell (bacterial cell, fungal cell, plant cell, animal cell, and so on) such as materials derived from biological origin, biological sample and the like. The culture solution is a culture medium in which microorganisms, cells or tissues have been cultured. In addition, in the nucleic acid-containing solution after enzyme reaction, the enzyme reaction means, but not limited to, an enzyme reaction in which nucleic acid is involved as a substrate, and nucleic acid or fragment thereof is contained in the resulting reaction solution. For example, enzyme reactions using an enzyme such as restriction enzyme, reverse transcriptase, DNA polymerase are included.

In the present invention, the above-described nucleic acid is preferably GC-rich nucleic acid. Here, "GC-rich nucleic acid" means a nucleic acid abundant in G and C, in other word, a nucleic acid with high GC-content, and particularly, a nucleic acid comprising GC-rich sequence corresponds to the category. GC-content is, when nucleotide composition of nucleic acid is concerned, represented by a proportion (%) of G and C in the total composition. The GC-content of DNA is different for different living organism, and in higher animals, the value is in a narrow range centering around 42%. Most of nucleic acids comprising high level of G and C are considered to be basic nucleic acid which is essential for cell survival. The GC-rich sequence means, in the nucleotide sequence of the target nucleic acid, a sequence with partially high content of G (guanine) and C (cytosine). More specifically, the GC-content is 60% or more, preferably 70% or more, and particularly preferably 80% or more. For example, "CpG Island" commonly found in promoter region of gene can be exemplified. However, the sequence of guanine (G) and cytosine (C) is not necessarily adjacent as seen in the CpG Island.

According to the method for isolating nucleic acid of the present invention, by selecting a "protein having a capability of binding nucleic acid" as a "nucleic acid-binding protein" in advance, nucleic acid or the fragment thereof which comprises specific nucleotide sequence to be recognized by the nucleic acid-binding protein can be searched for as a nucleic acid capable of binding with the protein. In this case, the nucleic acid for binding may be bound sometimes based on a non-specific interaction, but may be nucleic acid having a specific protein-binding site.

A preferable embodiment of the method for isolating nucleic acid of the present invention is characterized in that, the nucleic acid extracted after cell lysis by disruption of cell membrane of cell contained in the specimen derived from biological origin, culture solution or cell containing solution, the nucleic acid extracted from running gel (for example, agarose gel, polyacrylamide gel, and the like) after electrophorosis, or the nucleic acid in a nucleic acid containing solution after enzyme reaction is contacted with the above-described solid support, and thereby, allowed to be bound with the MDP1 on the surface of the solid support, and then the nucleic acid is recovered and purified. In a further preferable embodiment, the nucleic acid bound to MDP1 on the surface of the magnetic solid support can be separated by conducting the solid-liquid separation by use of magnet or a magnetic sorting machine from cell, membrane, the other intracellular elements, agarose gel or polyacrylamide gel components, or contaminants such as protein, and further from the dissolution buffer containing chemical reagents, and the desired nucleic acid can be separated and purified. In the purification of nucleic acid by this method, in the operations of washing the solid support with nucleic acid trapped, elution of trapped nucleic acid from the solid support, the solid-liquid separation by using magnetic action is carried out as an alternative for centrifugal separation, filtration, decantation and so on. As this method does not include operations such as centrifugal separation, filtration and treatment under reduced pressure, isolation and purification of nucleic acid can be performed easily and speedy.

A preferable embodiment of the present invention includes, a method for purifying nucleic acid from a sample containing pathogenic bacterial cell by combination of the above-described methods of isolation of cell, extraction of nucleic acid, and purification of the nucleic acid, that a method for isolating nucleic acid comprising a step to isolate cell in which the solid support comprising a polypeptide having a binding capability with mycolic acid-containing glycolipid which is immobilized on the surface thereof is contacted with a sample containing a bacterial cell having mycolic acid-containing glycolipid in the cell wall, a step in which nucleic acid in the isolated bacterial cell is extracted, and a step in which the solid support comprising a polypeptide having a binding capability with nucleic acid which is immobilized on the surface thereof is contacted with a sample containing nucleic acid. According to the present method, extraction of nucleic acid or purification of the extracted nucleic acid can be performed continuously in the state of anchoring on the solid support. As preferable procedures in each step of isolation of cell, extraction of nucleic acid and purification of nucleic acid are as described above, explanation of them is skipped here.

A preferable embodiment of the present invention includes a method for purifying nucleic acid, in which after pathogenic acid-fast bacterial cells are bound with MDP1 on the solid support, the bound cells are lysed by physical method or chemical method to release nucleic acid, and the nucleic acid is separated by binding with the MDP1 on the solid support. As to the solid support for use in purification of the nucleic acid, the solid support once used for the isolation of cell may be used again for purification of nucleic acid, or another solid support may be used. That is, an embodiment may be that once the cells contained in a sample are bound to the solid support, then the nucleic acid released by cell lysis is recovered on the same or another solid support.

The magnetic solid support binding with the above-described pathogenic acid-fast bacteria is suspended in dissolution buffer, and if necessary, the cell membrane is disrupted by further denaturation treatment such as heating or ultrasonication. The nucleic acid, released from the cell and bound to MDP1 on the surface of the magnetic solid support, is separated by conducting the solid-liquid separation by the above-described methods from cell membrane, the other intracellular elements, and further from the dissolution buffer containing chemical reagents, and the desired nucleic acid can be isolated. However, for specific method in each step of isolation of cell, extraction of nucleic acid and purification of nucleic acid, any of the above-described method can be employed without limiting to the above-described embodiment. Since this method does not include operations such as centrifugal separation, filtration and treatment under reduced pressure, isolation and purification of nucleic acid can be performed easily and speedy.

In the case where, after nucleic acid is extracted by the present method, a step of extraction of objective nucleic acid by electrophoresis and the like is included, solubilization of agarose gel used for the electrophoresis can be performed by known chemical reagent and heat treatment. In the method of the present invention, use of PCR purification kit (Promega) and heat treatment at 60° C. is preferable. In this regard, conditions, under which MDP1 on the solid support traps effectively the nucleic acid released after extraction of nucleic acid, has to be set. Prior to this step, for example, the above-described dissolution buffer used for the disruption of cell membrane, agarose gel solubilization solution or enzyme reaction solution may be removed, by dialyzing whole suspension containing solid support. The nucleic acid remained by binding with MDP1 on the solid support is washed to remove undesired substances, then the nucleic acid purified by dissociation from solid support can be applied directly to DNA amplification reaction, hybridization, restriction enzyme reaction, detection reaction or electrophoretic analysis, and so on. Therefore, even if the sample is trace amount, high-purity nucleic acid can be isolated from cells in high yield, according to the method of the present invention. Specifically, the above-described cell membrane disruption treatment is effective treatment condition for bacteriolysis, and also the agarose solubilization treatment is an effective treatment for agarose, which are at least within the range where the released nucleic acid does not cause denaturation. To release the nucleic acid from solid support, solvent or buffer with low ionic strength is applied to the solid support, if necessary, on heating. Temperature for releasing nucleic acid is, preferably 50 to 90°C., more preferably 70 to 80'C. For such elution liquid, water, Tris-HCl buffer, phosphate buffer and the like are exemplified. The eluted nucleic acid may be recovered by removing the solid support by way of the above-described solid-liquid separation operation and the like.

The nucleic acid obtained by the above-described method for purifying nucleic acid can be used for DNA amplification reaction such as PCR, SDA, LCR, LAMP, TMA, TAS, 3SR and NASBA, or for use in the analysis such as, for example, determination of nucleotide sequence, hybridization method and Southern blot analysis.

The method for isolating nucleic acid of the present invention is not limited to the above-described specific description, and it goes without saying that the method is available on the occasion of conducting isolation and purification based on the binding between arbitrary nucleic acid-binding protein and arbitrary nucleic acid.

[Kit]

A kit, involved in the present invention comprises a solid support in which a polypeptide having a binding capability with mycolic acid-containing glycolipids and/or nucleic acid is immobilized on the surface of the carrier. The kit may be used for the method for isolating cell, the method for extracting nucleic acid, or the method for isolating nucleic acid or the method for isolating nucleic acid in combination of these methods of the present invention. Therefore, the kit may comprise, in addition to the solid support of the present invention, a set of apparatus and materials necessary for practicing the method of the present invention, particularly, various kinds of reagents, solid support (preferably, a solid support comprising magnetic carrier), and apparatus necessary for isolating cell, extracting and purifying nucleic acid. In these reagents, dissolution (or dilution) liquid for dissolving (or diluting) sample, washing solution, various kinds of buffer solutions and the like are also included. In a preferable embodiment of the kit, the magnetic beads for practicing the method of the present invention, binding buffer, cell wash buffer (cell wash liquid), dissolution buffer (resuspension liquid), nucleic acid wash buffer (nucleic acid wash liquid), nucleic acid elution buffer (elution liquid) are each encapsulated in a container in advance. In a set of necessary apparatus and materials, a dedicated apparatus for use in further adsorbing or binding cells to the solid support, disrupting the cells and extracting nucleic acid contained therein may be included. Using these apparatus, the above-described method for extracting and purifying nucleic acid of the present invention can be practiced.

For practicing the method of the present invention described later, devices or apparatus other than the above-described ones may be sometimes needed, and these may be included appropriately as a constituent of the kit of the present invention. For the solid-liquid separation, a magnetic sorting machine is used, but centrifugal separator may also be used, and in such occasion, a compact centrifugal separator or the like is used.

In the method for isolating cell or the method for extracting nucleic acid of the present invention, at least 2 kinds of buffer solution are used. The binding buffer includes phosphate type, acetate type, Tris type or HEPES type of buffer solutions which may contain sodium chloride or potassium acetate as a salt, EDTA, surface active agent and so on, and for example, PBS, TBS, and HBS can be exemplified. For the wash buffer, solutions obtained by diluting the above-described binding buffer by 4 to 5 times may be used, but a different type of buffer may also be prepared separately. As the dissolution buffer, water or buffer solution, or a buffer solution containing salts are exemplified, and in particular TE buffer solution's suitable. As described above, the present kit preferably does not comprise organic solvent such as chloroform and phenol, chaotropic reagents, bacteriolytic agents used to be used for extraction of nucleic acid in the conventional art, but these reagents may be suitably employed, if necessary.

In addition, in the method for purifying nucleic acid in combination of the above-described methods of isolation of cell, extraction of nucleic acid and purification of nucleic acid from a sample containing pathogenic bacterial cell, at least 4 kinds of buffer solutions are used. The binding buffer includes phosphate type, acetate type, Tris type or HEPES type of buffer solutions which may contain sodium chloride or potassium acetate as a salt, EDTA, surface active agent and so on, and for example, PBS, TBS, and HBS can be exemplified. For the cell wash buffer, solutions obtained by diluting the above-described binding buffer by 4 to 5 times may be used, but a different type of buffer may also be prepared separately. As the dissolution buffer, PBS, TBS, and HBS and the like containing SDS and the like are exemplified, and particularly, the one which is optimal for binding nucleic acid with MDP1 is suitable. For the nucleic acid wash buffer, solutions obtained by diluting the above-described dissolution buffer by 4 to 5 times may be used, but a different type of buffer may also be prepared separately. As a nucleic acid dissolution buffer, water or buffer solution, or a buffer solution containing salts are exemplified, and in particular TE buffer solution is suitable. As described above, the present kit preferably does not comprise organic solvent such as chloroform and phenol, chaotropic reagent, bacteriolytic agent used to be used for extraction of nucleic acid in the conventional art, but these reagents may be suitably employed, if necessary.

A dedicated kit for the method for extracting and purifying nucleic acid of the present invention is made up from a set of necessary apparatus and reagents. It is preferable that either of the apparatus is made up normally as a consumable only for single analysis. It is also preferable that containers to be used for containing buffer and the like are sterilized previously to prevent bacterial contamination.

On the occasion when the method of the present invention is practiced, together with the above-described consumables, mixer for stirring, stirring bar, heater for heating or ultrasonic wave generator, magnet for use in solid-liquid separation by magnetic treatment, magnetic sorting machine and the like are also used. In particular, stirring is preferably vibration by test tube mixer or tumble mixing by rotation of container, and the magnet may be a bar-magnet. Type of magnet may be either electric magnet or permanent magnet, but permanent magnet is preferable from the viewpoints of simplicity and operability, and in particular, neodymium magnet is preferable due to strength of magnetic force.

These are instruments commonly equipped in a clinical laboratory, and the method of the present invention can be practiced using these instruments together with the present kit. Further, if necessary, a part of these instruments may be included as a constituent of the kit. As to the above-described solid support and an entire or a part of the kit, as long as structure, composition, layout, shape and configuration, dimension, quality of material, principle and method may be widely varied, so long as these conform to the purpose of the present invention.

In the case where, a specific "nucleic acid-binding protein" is selected in advance and "nucleic acid capable of binding the protein" is intended to be searched for, the "nucleic acid"

may be an arbitrary nucleic acid which is predictable to bind the above-described "nucleic acid-binding protein" by specific or nonspecific mode of action. In such aspect of the present invention, the method of the present invention may also be provided for efficient search of objective nucleic acid or specific gene utilizing the above-described kit and the method for isolating nucleic acid. In addition, the method of the present invention may also be utilized for screening of the compound, a protein or a reagent which targets DNA-protein interaction. In this case, an action influencing on the specific DNA-protein interaction can be evaluated by determining a quantity of bound DNA.

As an example of the method, there is en embodiment in which this method is utilized to search for DNA or gene having GC-rich nucleotide sequence. Most of products of genes having GC-rich sequence are of important physiological significance, such as cytokine, growth factor, kinase, and transcription factor. In addition, a methylation phenomenon of the above-described "CpG Island" is involved in the control of transcription activity and regulation of expression of gene. The phenomenon of CpG Island methylation may also be relevant to SNP (single nucleotide polymorphisms) analysis in relation to disorder and treatment. Further, in the known triplet which is involved in a disorder defined on a genetic level as "triplet repeat disease", a proportion of G and C is high. As described above, investigations and researches on DNA or gene ("GC-rich gene") having GC rich sequence and repeat sequences occupy a quite important position in the field such as genomic function and control, disorder, regenerative medicine, embryology and aging. Nevertheless, the research of nucleic acid and genes having GC-rich nucleotide sequence faces to several obstacles such as low amplification efficiency, restriction on primer, impediment in nucleotide sequence analysis, low translation efficiency and low SNP detection efficiency, due to rigid secondary structure and high homology because of low sequence polymorphism. The method for purification and the kit of the present invention allow easy screening and isolation of GC-rich nucleic acid because of utilizing MDP1 and the like capable of recognizing G, C nucleotide, and are useful for search and identification of specific gene.

EXAMPLES

Hereinafter, embodiment of the present invention will be further explained in detail by referring to the following Examples and Comparative Example, but the technical scope of the present invention should not be limited thereto.

Example 1

<Preparation of MDP1 and its Immobilization on Magnetic Beads>
(MDP1 Protein)

MDP1 protein (hereinafter, referred to as "MDP1") was prepared from BCG Tokyo strain (hereinafter, referred to as "BCG") according to the method described in WO 2000/44905. General description is as follows.

The BCG was resuspended in 50 ml of TNNSH (10 mM Tris-HCl, pH 7.5, 10 mM $MgCl_2$, 60 mM $NH_4Cl$, and 6 mM 2-mercaptoethanol), and disrupted by ultrasonication. The pellet obtained by centrifugation at 30,000×g for 2 hours was resuspended in 0.25 N HCl by stirring overnight at 4° C., then centrifuged at 20,000×g for 20 minutes. To the supernatant solution, 0.1 times volume of 100% (w/v) TCA was added under vigorous stirring. The precipitate formed by standing at 4° C. for 4 hours was recovered by centrifugation, and washed once with acidic acetone prepared by adding 0.01ml of concentrated hydrochloric acid into acetone (20 ml), then washed twice with acetone, and then dried in a vacuum desiccator. The dried precipitate was resuspended in 0.2 M sodium phosphate buffer (pH 6.8). Next, acid soluble protein was subjected to chromatography using Fast Flow column (bed volume, 5 ml; HITRAP CM FF, GE Healthcare Bio-Science AB) and fractionated by elution with linear gradient concentration of guanidine hydrochloride (GdnCl) in 0.2 M sodium phosphate buffer (pH 6.8) at room temperature. The gradient was produced by a concentration-gradient generator filled with each 0% and 5% GdnCl (15 ml). Flow rate was kept at 1 ml/min, and eluting solution was collected by each 1 ml of fractions. Fraction containing purified MDP1 was dialyzed against 0.2 M phosphate buffer containing 5% GdnCl, and concentrated. At the end, the concentrate was further purified by a gel filtration chromatography column HILOAD 16/60 SUPERDEX 200 pg, GE Healthcare Bio-Science AB). Purity of the protein was monitored by determining absorbance at 220 nm or by analysis on SDS-PAGE.

MDP1 was immobilized by binding covalently through amino group in MDP1 with epoxy group of the epoxy-group-activated beads of magnetic beads (DYNABEADS M-270, Invitrogen Corp.), (MDP1-Epoxy BEADS). Quantity of immobilized MDP1 protein was 1 to 1.5 ug/1 mg BEADS.
(Recombinant MDP1 protein)

Histidine-tagged recombinant MDP1 (rMDP1) was prepared according to the method reported previously (Aoki et al., J. Biol. Chem., 279; 39798-39806 (2004)). General description is as follows.

Firstly, rMDP1 expression vector (pET22B-MDP1) was introduced into competent E. coli cell (BL21 (DE3) pLysS competent cells, Invitrogen Corp.) and transformed. This transformation was cultured in LB liquid medium containing 50 μg/ml of carbenicillin and 34 μg/ml of chloramphenicol at 22° C., and when the absorbance at 600 nm reached to 0.3 to 0.6, IPTG (isopropyl-1-thio-β-D-glactopyranoside) was added. By culturing for 16 hours, rMDP1 was expressed.

The E. coli cells recovered by centrifugation were disrupted by ultrasonic treatment using ultrasonic-type cell disruption equipment (BIORUPTOR UCD-2000T (ultrasonic ell disruptor), TOSOH Corp.), and centrigued again at 8,000×g for 30 minutes, and then the supernatant solution was recovered as a dissolved protein. This supernatant solution was passed through a membrane filter (0.22 μm) to remove foreign particles and the like, and then added to a carrier for metal chelation affinity chromatography (Ni-NTA Agarose, QIAGEN K.K.) equilibrated with 50 mM solution dihydrogen phosphate (pH 8.0), 10 mM imidazole, 0.5 M NaCl and 0.01% TWEEN (surfactant). After nonspecifically adsorbed proteins were removed by washing the column, rMDP1 was eluted by eluent buffer comprising 50 nM sodium dihydrogen phosphate (pH 8.0), 300 mM imidazole, 0.5 M Na Cl and 0.01% TWEEN (surfactant). After that, the eluent buffer was replaced with PBS by dialysis. After SDS-PAGE, concentration of rMDP1 was measured by staining with Coomassie Brilliant Blue (CBB), and as a result, concentration of obtained rMDP1 was 1 mg/ml.

The rMDP1 was immobilized on the magnetic beads of BD TALON (DYNABEADS M-TALON (magnetic beads), Invitrogen Co.) by coordinate bond through histidine tag (rMDP1-His-TALON BEADS). Quantity of immobilized rMDP1 protein was 30 μg/1 mg BEADS.

Example 2

Recovery of Tuberculosis Bacteria (BCC) Using MDP1 and rMDP1 Immobilized Magnetic Beads A 50 µl of luciferase expressing BCG (BCG-Luc) solution (5×10$^4$ cfu) was mixed by stirring with 7.5 µg of MDP1-Epoxy BEADS or rMDP1-His-TALON BEADS suspended with binding buffer (PBS). On the side, the same amount of BCG-Luc was mixed by stirring in 50 µl with 7.5 µg of magnetic beads of BUGS' n BEADS version TB (Genpoint AS) under the recommended condition of solution. After standing at 25° C. for 15 minutes, the magnetic beads and the supernatant solution were separated using a magnetic sorting machine, and thereby BCG-Luc was recovered on the magnetic beads. Recovery efficiency of the BCG-Luc was calculated by determination of cell number using Luciferase assay kit (Promega Corp.). The results are shown in Table 1.

TABLE 1

| Magnetic beads | Recovered bacterial number (cfu) | Recovery efficiency (%) |
|---|---|---|
| MDP1-Epoxy BEADS | 1.4 × 10$^4$ | 28 |
| rMDP1-His-TALON BEADS | 2.6 × 10$^4$ | 52 |
| BUGS' n BEADS | 0.65 × 10$^4$ | 13 |

Harvest efficiency of MDP1-Epoxy BEADS showed 2 times or more of that of Genpoint's magnetic beads (BUGS' n BEADS) (magnetic beads). In addition, harvest efficiency of rMDP1-His-TALON BEADS showed 4 times or more of that of Genpoint's magnetic beads.

Example 3

Recovery of Tuberculosis Bacteria (BCG) and Extraction of Nucleic Acid Using MDP1-Immoblized Magnetic Beads A 50 µl of BCG solution (7.5×10$^4$ cfu) was mixed by stirring with 7.5 µg of MDP1-Epoxy BEADS suspended with binding buffer (PBS). On the side, the same amount of BCG was mixed by stirring in 50 µl with 7.5 µg of magnetic beads of BUGS' n BEADS version TB (Genpoint AS) under the recommended condition of solution. After standing at 25° C. for 15 minutes, the magnetic beads and the supernatant solution were separated using a magnetic sorting machine, and thereby BCG was recovered on the magnetic beads. Next, the recovered BCG was resuspended in 50 µl of dissolution buffer (TE), and treated by ultrasonication of 28 kHz at 25° C. for 10 minutes, and thereby, cells were lysed, and DNA was extracted. The obtained DNA was subjected to quantitative PCR, and extraction efficiencies of nucleic acid were compared. The quantitative PCR was carried out using a *Mycobacterium* nucleic acid kit COBAS TAQMAN MTB (*Mycobacterium* nucleic acid kit), Roche Diagnostic Corp.). Extraction efficiency of nucleic acid was calculated by assuming the recovery efficiency by the BUGS' n BEADS (magnetic beads) as 1. The results are shown in Table 2.

TABLE 2

| Magnetic beads | Copy number of amplified region in recovered nucleic acid (copies) | Extraction efficiency of nucleic acid (arbitrary unit) |
|---|---|---|
| MDP1-Epoxy BEADS | 2.63 × 10$^7$ | 3.2 |
| BUGS' n BEADS | 0.82 × 10$^7$ | 1 |

The extraction efficiency of nucleic acid by MDP1 magnetic beads were 3 times or more as compared with that by Genpoint's magnetic beads.

Example 4

Purification of Nucleic Acid Using MDP1-Immobilized Magnetic Beads

A 50 µl of plasmid DNA solution (2×10$^6$ copies/µl) was added to 7.5 µl of MDP1-Epoxy BEADS of Epoxy BEADS having no immobilized MDP1 (10 mg/ml) which were suspended with binding buffer (PBS), and mixed by stirring, and then left at 25° C. for 15 minutes. After that, the supernatant solution was separated using a magnetic sorting machine and recovered in a new tube (Sup). On the other hand, after DNA-magnetic beads complex was washed with wash buffer (PBS), resuspended in 50 µl of eluent buffer (MilliQ water+ 0.005% SDS), and then the DNA was eluted by heating at 98° C. for 5 minutes (Elute). The obtained DNA solution (Sup, Elute) was subjected to quantitative PCR, and recovery of the nucleic acid was calculated. The quantitative PCR was carried out using a *Mycobacterium* nucleac acid kit COBAS TAQMAN MTB (*Mycobacterium* nucleic acid kit), Roche Diagnostics Corp.). The results are shown in Table 3.

| Magnetic beads | Sup [copies] (Unbound DNA) | Elute [copies] (Recovered DNA) | Recovery [%] |
|---|---|---|---|
| MDP1-Epoxy BEADS | 7.15 × 10$^5$ | 5.05 × 10$^7$ | 50.5 |
| Epoxy BEADS | 4.57 × 10$^7$ | N/D | N/D |

Using MDP1-immobilized magnetic beads, nucleic acid was able to be recovered.

The present application is based on Japanese Patent Application. No. 2007-300506 filed on Nov. 20, 2007 and Japanese patent Application No. 2008-001616 filed on Jan. 8, 2008, and the disclosures in both applications are incorporated herein in entirety by reference.

What is claimed is:

1. A method for isolating a bacterial cell having mycolic acid-containing glycolipid in a cell wall from a sample containing the bacterial cell, comprising the steps of:
   contacting the sample containing the bacterial cell having the mycolic glycolipid in the cell wall with a polypeptide immobilized on a surface of a magnetic carrier, wherein the polypeptide is *Mycobacterium* DNA-Binding Protein 1 (MDP1) to bind the bacterial cell having the mycolic acid-containing glycolipid in the cell wall to the polypeptide immobilized on the surface of the magnetic carrier; and
   separating the bacterial cell having the mycolic acid-containing glycolipid in the cell wall bound to polypeptide immobilized on the surface of the magnetic carrier from the sample.

2. The method of Claim 1 wherein the bacterial cell is *mycobacterium tuberculosis*.

3. The method of claim 1, wherein the magnetic carrier is magnetic beads.

4. A method for extracting a nucleic acid, comprising the steps of:
   contacting a sample containing a bacterial cell having mycolic acid-containing glycolipid in a cell wall with a polypeptide immobilized on a surface of a magnetic carrier to isolate the bacterial cell from the sample, wherein the polypeptide is *Mycobacterium* DNA-Binding Protein (MDP1); and
   extracting the nucleic acid from the isolated bacterial cell.

5. The method of claim 4 wherein the extracting step further comprises a step of lysing the isolated bacterial cell by heating, ultrasonic treatment, or chemical treatment to release the nucleic acid.

6. The method of claim 4, wherein the magnetic carrier is magnetic beads.

7. A method for isolating a nucleic acid, comprising the steps of:
   contacting a sample containing a bacterial cell having mycolic acid-containing glycolipid in a cell wall with a polypeptide immobilized on a surface of a magnetic carrier to isolate the bacterial cell from the sample, wherein the polypeptide is *Mycobacterium* DNA-Binding Protein (MDP1);
   extracting the nucleic acid from the isolated bacterial cell and forming a sample containing the nucleic acid;
   contacting a polypeptide immobilized on a surface of a magnetic carrier with the sample containing nucleic acid, wherein the polypeptide is *Mycobacterium* DNA-Binding Protein (MDP1) to bind the nucleic acid to the polypeptide immobilized on the surface of the magnetic carrier; and
   separating the nucleic acid bound to the polypeptide immobilized on the surface of the magnetic carrier from the sample.

8. The method of claim 7 wherein the step of separating is a solid-liquid separation utilizing magnetic action.

9. The method of claim 7, wherein the nucleic acid has a GC-rich sequence.

10. The method of claim 7, wherein the magnetic carrier is magnetic beads.

11. The method of claim 7, wherein the extracting step further comprises a step of lysing the isolated bacterial cell by heating, ultrasonic treatment, or chemical treatment to release the nucleic acid.

* * * * *